United States Patent
Wang et al.

(10) Patent No.: US 11,464,779 B2
(45) Date of Patent: *Oct. 11, 2022

(54) PHARMACEUTICAL FORMULATION OF PALBOCICLIB AND A PREPARATION METHOD THEREOF

(71) Applicant: Shenzhen Pharmacin Co., Ltd., Shenzhen (CN)

(72) Inventors: Zeren Wang, Southbury, CT (US); Jun Xu, Newtown, CT (US); Long Qu, Shenzhen (CN)

(73) Assignee: Shenzhen Pharmacin Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/024,389

(22) Filed: Sep. 17, 2020

(65) Prior Publication Data

US 2021/0000835 A1    Jan. 7, 2021

Related U.S. Application Data

(63) Continuation of application No. 16/554,112, filed on Aug. 28, 2019, now Pat. No. 10,813,937, which is a continuation of application No. 15/613,853, filed on Jun. 5, 2017, now Pat. No. 10,449,195, which is a continuation of application No. PCT/CN2016/086546, filed on Jun. 21, 2016.

(30) Foreign Application Priority Data

Mar. 29, 2016    (CN) .......................... 201610187046.8

(51) Int. Cl.
| | | |
|---|---|---|
| *A61K 31/519* | (2006.01) | |
| *C07D 471/04* | (2006.01) | |
| *A61K 9/48* | (2006.01) | |
| *A61K 9/14* | (2006.01) | |
| *A61K 9/16* | (2006.01) | |

(52) U.S. Cl.
CPC ............ *A61K 31/519* (2013.01); *A61K 9/146* (2013.01); *A61K 9/1652* (2013.01); *A61K 9/4808* (2013.01); *C07D 471/04* (2013.01)

(58) Field of Classification Search
CPC .... A61K 31/519; A61K 9/146; A61K 9/1652; A61K 9/4808; C07D 471/04
See application file for complete search history.

(56) References Cited

U.S. PATENT DOCUMENTS

| | | | |
|---|---|---|---|
| 745,168 A | 11/1903 | Eastwood | |
| 4,696,745 A * | 9/1987 | Itagaki ..................... | C08F 8/18 210/198.2 |
| 4,847,092 A | 7/1989 | Thakkar et al. | |
| 6,087,380 A | 7/2000 | Hauel et al. | |
| 6,936,612 B2 | 8/2005 | Barvian et al. | |
| 7,022,711 B2 | 4/2006 | Hamby et al. | |
| 7,208,489 B2 | 4/2007 | Barvian et al. | |
| 7,345,171 B2 | 3/2008 | Beylin et al. | |
| 7,456,168 B2 | 11/2008 | Barvian et al. | |
| 7,863,278 B2 | 1/2011 | Beylin et al. | |
| 7,866,474 B2 | 1/2011 | Geser et al. | |
| 7,932,273 B2 | 4/2011 | Schmid et al. | |
| 8,557,995 B2 | 10/2013 | Miller et al. | |
| 8,669,257 B2 | 3/2014 | Liu et al. | |
| 9,034,822 B2 | 5/2015 | Van Ryn et al. | |
| 9,259,399 B2 | 2/2016 | Chen-Kiang et al. | |
| 9,889,135 B2 | 2/2018 | Koff et al. | |
| 9,925,174 B2 | 3/2018 | Brauns et al. | |
| 10,160,759 B2 | 12/2018 | Wu et al. | |
| 10,258,604 B2 | 4/2019 | Andreano et al. | |
| RE47,739 E | 11/2019 | Barvian et al. | |
| 2003/0149001 A1 | 8/2003 | Barvian et al. | |
| 2005/0019399 A1 | 1/2005 | Fischer et al. | |
| 2007/0015802 A1 | 1/2007 | Lal et al. | |
| 2007/0141141 A1 | 6/2007 | Bateman et al. | |
| 2009/0030005 A1 | 1/2009 | Kamb et al. | |
| 2009/0214645 A1 | 8/2009 | Kramer et al. | |
| 2011/0009353 A1 | 1/2011 | Chen-Kiang et al. | |
| 2011/0030662 A1 | 2/2011 | Zitzler et al. | |
| 2011/0306632 A1 | 12/2011 | Miller et al. | |
| 2014/0220112 A1 | 8/2014 | Szoka, Jr. et al. | |

(Continued)

FOREIGN PATENT DOCUMENTS

| | | |
|---|---|---|
| CN | 1638771 A | 7/2005 |
| CN | 101410093 A | 4/2009 |

(Continued)

OTHER PUBLICATIONS

English translation of CN 106474129 A, pp. 1-16, publ. Mar. 8, 2017 (Year: 2017).*
Affymetrix GeneChip Human Genome U133 Array Set HG-U133A, Geo Expression, Mar. 11, 2002 (XP002361324).
Babic, S. et al. Determination of pKa Values of active pharmaceutical ingredients. Trends in Analytical Chemistry, 26(11):1043-1061 (2007).
Barvian, M., et al., "Pyrido[2,3-d]pyrimidin-7-one Inhibitors of Cyclin-Dependent Kinases" J. Med. Chem. (2000), 43, pp. 4606-4616.
Baselga, Jose et al., Everolimus in Postmenopausal Hormone-Receptor-Positive Advanced Breast Cancer, New England Journal of Medicine, Massachusetts Medical Society, US, vol. 366, No. 6, Feb. 9, 2012 (Feb. 9, 2012), pp. 520-529, XP002684647, ISSN: 0028-4793, DOI: 10.1056/NEJMOALL09653.

(Continued)

*Primary Examiner* — Sarah Pihonak
(74) *Attorney, Agent, or Firm* — Wilson Sonsini Goodrich & Rosati

(57) ABSTRACT

The present invention belongs to the pharmaceutical field, and in particular, it relates to a pharmaceutical formulation of palbociclib and a preparation method thereof. The pharmaceutical formulation comprises palbociclib, an acidic auxiliary material, and optionally a hydrophilic high-molecular material, which has better solubility and in vitro dissolution property as compared with the conventional formulation and can be used for enhancing in vivo absorption and bioavailability of palbociclib.

20 Claims, 5 Drawing Sheets

(56) References Cited

U.S. PATENT DOCUMENTS

| | | |
|---|---|---|
| 2014/0309250 A1 | 10/2014 | Verma et al. |
| 2015/0099737 A1 | 4/2015 | Brain et al. |
| 2015/0111896 A1 | 4/2015 | Sharpless et al. |
| 2015/0140036 A1 | 5/2015 | Mannick et al. |
| 2015/0273070 A1 | 10/2015 | Li et al. |
| 2016/0310482 A1 | 10/2016 | Haber et al. |
| 2017/0281631 A1 | 10/2017 | Wang et al. |
| 2018/0098963 A1 | 4/2018 | Andreano et al. |
| 2018/0207100 A1 | 7/2018 | Ibrahim et al. |
| 2018/0280392 A1 | 10/2018 | Zeng et al. |
| 2019/0046533 A1 | 2/2019 | Chen et al. |
| 2019/0091227 A1 | 3/2019 | Czibere et al. |
| 2019/0120844 A1 | 4/2019 | Lou et al. |
| 2019/0231718 A1 | 8/2019 | Andreano et al. |
| 2019/0292605 A1 | 9/2019 | Slamon et al. |
| 2019/0345558 A1 | 11/2019 | Raspe et al. |
| 2019/0381051 A1 | 12/2019 | Wang et al. |

FOREIGN PATENT DOCUMENTS

| | | | |
|---|---|---|---|
| CN | 101632668 A | | 1/2010 |
| CN | 1835951 B | | 6/2010 |
| CN | 101001857 B | | 6/2011 |
| CN | 102106806 A | | 6/2011 |
| CN | 102106807 A | | 6/2011 |
| CN | 101906104 B | | 6/2013 |
| CN | 104224754 A | | 12/2014 |
| CN | 104434809 A | | 3/2015 |
| CN | 104887641 A | | 9/2015 |
| CN | 105085517 A | | 11/2015 |
| CN | 105213322 A | | 1/2016 |
| CN | 105616418 A | | 6/2016 |
| CN | 105616419 A | | 6/2016 |
| CN | 105816437 A | | 8/2016 |
| CN | 106474129 A | * | 3/2017 |
| CN | 106667952 A | | 5/2017 |
| CN | 106794183 A | | 5/2017 |
| CN | 106831710 A | | 6/2017 |
| CN | 106967061 A | | 7/2017 |
| CN | 107510847 A | | 12/2017 |
| CN | 107666914 A | | 2/2018 |
| CN | 107759594 A | | 3/2018 |
| CN | 108014343 A | | 5/2018 |
| CN | 108017629 A | | 5/2018 |
| CN | 108066303 A | | 5/2018 |
| CN | 108272754 A | | 7/2018 |
| CN | 108653222 A | | 10/2018 |
| CN | 108864078 A | | 11/2018 |
| CN | 105748435 B | | 3/2019 |
| CN | 110099680 A | | 8/2019 |
| CN | 110573183 A | | 12/2019 |
| CN | 106794182 B | | 2/2020 |
| CN | 108066312 B | | 3/2020 |
| CN | 110997666 A | | 4/2020 |
| EP | 0962443 A1 | | 12/1999 |
| EP | 1648889 B1 | | 10/2008 |
| EP | 3255046 B1 | | 10/2018 |
| EP | 3302565 B1 | | 11/2019 |
| IN | 7086CHE2015 | | 12/2015 |
| IN | 20164100225 | | 3/2016 |
| JP | 2000309588 A | | 11/2000 |
| JP | 2008536913 A | | 9/2008 |
| JP | 2013528218 A | | 7/2013 |
| WO | WO-0155148 A1 | | 8/2001 |
| WO | WO-2001707041 | | 9/2001 |
| WO | WO-03062236 A1 | | 7/2003 |
| WO | WO-03074056 A1 | | 9/2003 |
| WO | WO-2005005426 A1 | | 1/2005 |
| WO | WO-2006112649 A1 | | 10/2006 |
| WO | WO-2010055119 A2 | | 5/2010 |
| WO | WO-2011063309 A1 | | 5/2011 |
| WO | WO-2011156361 A2 | | 12/2011 |
| WO | WO-2014011398 A1 | | 1/2014 |
| WO | WO-2014128588 A1 | | 8/2014 |
| WO | WO-2015022609 A1 | | 2/2015 |
| WO | WO-2015160986 A2 | | 10/2015 |
| WO | WO-2015165571 A2 | | 11/2015 |
| WO | WO-2016015598 A1 | | 2/2016 |
| WO | WO-2016127963 A1 | | 8/2016 |
| WO | WO-2016156070 A1 | | 10/2016 |
| WO | WO-2016193860 A1 | | 12/2016 |
| WO | WO-2017036390 A1 | | 3/2017 |
| WO | WO-2017115315 A1 | | 7/2017 |
| WO | WO-2017130219 A1 | | 8/2017 |
| WO | WO-2017211788 A1 | | 12/2017 |
| WO | WO-2018071440 A1 | | 4/2018 |
| WO | WO-2018191950 A1 | | 10/2018 |
| WO | WO-2019178239 A1 | | 9/2019 |
| WO | WO-2019220253 A1 | | 11/2019 |

OTHER PUBLICATIONS

Baughn, Linda et al., A novel orally active small molecule potently induces G1 arrest in primary, myeloma cells and prevents tumor growth by specific inhibition of Cdk4/6, Blood, vol. 108, No. 11, Part 1, Nov. 2006 (Nov. 2006), pp. 113A-114A, XP002509897 & 48th. Annual Meeting of the American-Society of Hematology, Orlando, FL, USA; Dec. 9-12, 2006 ISSN: 00064971.

Beeton, C. et al. Kv1.3 channels are a therapeutic target for T cell-mediated autoimmune diseases. PNAS 103(46):17414-17419 (Nov. 14, 2006).

Bhatia, Sangeeta et al., The challenges posed by cancer heterogeneity, Nature Biotechnology, vol. 30, No. 7, Jul. 2012, pp. 604-610.

Chuaprapaisilp, T. et al. Treatment of pustular psoriasis with clofazimine. Br. J. Dermatol. 99(3):303-305 (Sep. 1978).

Conalty, M.L. et al. The antileprosy agent B.663 (Clofazimine) and the reticuloendothelial system. Int. J. Lepr. Other Mycobact Dis. 39(2):479-492 (Apr.-Jun. 1971).

Conklin, Dylan Francis, Identification of Genomic Predictors of Response to the CDK4/6 Inhibitor Palbociclib using the UCLATORL Panel of Human Cancer Cell Lines, University of California, Los Angeles, PhD. Dissertation, 2013, 125 pages.

Curley, Michael D. et al., Seribantumab, an Anti-ERBB3 Antibody, Delays the Onset of Resistance and Restores Sensitivity to Letrozole in an Estrogen Receptor-Positive Breast Cancer Model, Molecular Cancer Therapeutics, vol. 14, No. 11, Nov. 1, 2015 (Nov. 1, 2015), pp. 2642-2652, XP055374862, US ISSN: 1535-7163, DOI: 1158/1535-7163.MCT-15-0169.

Dai Y, et al., Bortezomib and flavopiridol interact synergistically to induce apoptosis in chronic myeloid leukemia cells resistant to imatinib mesylate through both Bcr/Abl-dependent and -independent mechanisms, Blood Jul. 15, 2004 US, vol. 104, No. 2, Jul. 15, 2004 (Jul. 15, 2004), pp. 509-518, XP002509901 ISSN: 006-4971.

El-Deiry, Wafik S., Meeting report: The international conference on tumor progression and therapeutic resistance, Cancer Research, American Association for Cancer Research, American Association for Cancer Reearch, Baltimore, MD, US, vol. 65, No. 11, Jun. 1, 2005 (Jun. 1, 2005), pp. 4475-4484, XP002402154.

Ellis, BP et al. Clofazimine ointment in the treatment of trophic ulcers. S Afr Med J. 47(9):378-9 (Mar. 3, 1973).

EP Search Report for EP15875281.6 dated Jul. 9, 2018.

Final Office Action dated Jul. 1, 2019, for U.S. Appl. No. 15/613,853.

Final Office Action mailed May 4, 2020 for U.S. Appl. No. 16/554,103.

Final Office Action mailed May 4, 2020 for U.S. Appl. No. 16/554,112.

Finn, Richard S., et al., PD 0332991, a selective cyclin D kinase 4/6 inhibitor, preferentially inhibits proliferation of luminal estrogen receptor-positive human breast cancer cell lines in vitro, Breast Cancer Research, Current Science, London, GB, vol. 11, No. 5, Oct. 29, 2009 (Oct. 29, 2009), p. R77, XP021065288, ISSN: 1465-5411, DOI: 10.1186/BCR2419.

Fischer, Peter M. et al., Recent progress in the discovery and development of cyclin-dependent kinase inhibitors, Expert Opinion on Investigational Drugs Apr. 2005, GB, vol. 14, No. 4, Apr. 2005 (Apr. 2005), pp. 457-477, XP002509899 ISSN: 1354-3784.

Gartner, E.M. et al. The in vitro and in vivo effects of clofazimine on the motility of neutrophils and transformation of lymphocytes from normal individuals. Lepr Rev. Jun. 1982;53(2):85-90.

(56) References Cited

OTHER PUBLICATIONS

Huang, Y. et al. Fundamental aspects of solid dispersion technology for poorly soluble drugs. Acta Pharmaceutica Sinica B, 4(1):18-25 (2014).
Ibrance Drug Label Feb. 2018.
IBRANCE product insert, Pfizer Labs, Division of Pfizer Labs Inc., NY, NY 10017, Issued Feb. 2015, https://www.accessdata.fda.gov/drugsatfda_docs/label/2015/207103s000lbl.pdf.
International Search Report and Written Opinion (translated) dated Jan. 11, 2017 for PCT/CN2016/086546.
Kaiser, Cancer Genetics With an Edge, Science, AAAS, vol. 337, pp. 282-284 (2012).
Kelleher, D. et al. Preliminary trial of clofazimine in chronic inflammatory bowel disease. Gut. 1982, 23: A432-A463.
Leaf, Clifton, Why We're Losing the War on Cancer—and How to Win It, (2004) Fortune, Time Inc., pp. 1-26.
Lee, S.J. et al. Treatment of chronic graft-versus-host disease with clofazimine. Blood. 89(7):2298-2302 (Apr. 1, 1997).
Liu, Da David, MDM2 Levels Modulate the Cellular Senescence Response to CDK4 Inhibition, Dissertation Presented to the Faculty of the Cornell Graduate School, Mar. 2013, pp. 1-11.
Mackey, JP et al. Clofazimine in the treatment of discoid lupus erythematosus. Br. J. Dermatol. 91(1):93-96 (Jul. 1974).
Merck Millipore, ASK26/MDM2 Antibody Sampler Kit-Human.
Miller, Todd W., et al., ER[alpha]-dependent E2F transcription can mediate resistance to estrogen deprivation in human breast cancer, Cancer Discovery, American Association for Cancer Research, US, vol. 1, No. 4, Sep. 1, 2011 (Sep. 1, 2011), pp. 338-351, XP002683182, ISSN: 2159-8274, DOI: 10.1158/2159-8290.CD-11-0101.
Dragicevic, N. Eds., Percutaneous Penetration Enhancers Chemical Methods in Penetration Enhancement[M], Springer, 2015.
NCI, What is Cancer?, National Institutes of Health, Published Feb. 9, 2015, pp. 1-16.
Non-Final Office Action dated Dec. 20, 2019, for U.S. Appl. No. 16/554,103.
Non-Final Office Action dated Dec. 20, 2019, for U.S. Appl. No. 16/554,112.
Patani et al. Bioisosterism: A Rational Approach in Drug Design. Chem. Rev. 96:3147-3176 (1996).
Patel, VB et al. A topical dosage form of liposomal clofazimine: research and clinical implications. Pharmazie. 54(6):448-451 (Jun. 1999).
Podmore, P. et al. Clofazimine—an effective treatment for Melkersson-Rosenthal syndrome or Miescher's cheilitis. Clin Exp Dermatol. Mar. 1986;11(2):173-178.
Pradaxa Drug Label—Revised Mar. 2018; 27 pages.
Ren, Yunzhao R. et al. Clofazimine Inhibits Human Kv1.3 Potassium Channel by Perturbing Calcium Oscillation in T Lymphocytes. PLoS One 3(12):e4009:1-11 (2008).
Richard S Finn, et al., The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase study, The Lancet. Oncology, Jan. 1, 2015 (Jan. 1, 2015), pp. 25-35.
Rocca et al. expert opinion on pharmacotherapy, 2013, Taylor & Francis vol. 15(3), pp. 407-420.
Rocca, et al. Palbociclib (PD 0332991) : targeting the cell cycle machinery in breast cancer. Expert Opinion Pharmacother. Feb. 2014;15(3):407-20. Epub Dec. 26, 2013.
Sabbioni, et al., Biomonitoring of arylamines and nitroarenes Biomarkers, 2002, 7(5), pp. 347-421.
Schwartz, G.K., et al., Targeting the cell cycle: A new approach to cancer therapy, Journal of Clinical Oncology 2005 US, vol. 23, No. 36, 2005, pp. 9408-9421, XP002509900 ISSN: 0732-183X.
Shuangping, Yu et al., Progress in Surface Modification of Superfine Powder, Journal of Guangdong University of Technology, Jun. 30, 2003, pp. 70-76.
Slamon, Dennis J., 2013 Breast Cancer Highlight—Palbociclib (PD-0332991), a Breakthrough Therapy for Breast Cancer, Breast Cancer Research Program, Congressionally Directed Medical Research Programs, May 15, 2013 (May 15, 2013), pp. 1-2, XP055158107, Retrieved from the Internet: URL:http://cdmrp.army.mil/bcrp/research_highlights/13slamon_highlight.shtml.
Sun, W. et al., Impact of acid-reducing agents (ARAS) on the pharmacokinetics of palbociclib, a weak base with a ph-dependent solubility, under different food intake conditions, European Journal of Cancer, Dec. 31, 2015, XP055426702.
Sun, W. et al. Impact of acid-reducing agents (ARAS) on the pharmacokinetics of palbociclib, a weak base with ph-dependent solubility under differing food intake conditions, European Journal of Cancer, (Dec. 31, 2015), S59.
Sutherland, Robert L., et al., CDK inhibitors as potential breast cancer therapeutics: new evidence for enhanced efficacy in ER+ disease, Breast cancer research : BCR, Jan. 1, 2009 (Jan. 1, 2009), pp. 112-112, XP055145540, England DOI: 10.1186/bcr2454.
Toogood. Cyclin-dependent kinase inhibitors for treating cancer. Med Res Rev. Nov. 2001;21(6):487-98.
Toogood, et al., Discovery of a Potent and Selective Inhibitor of Cyclin-Dependent Kinase 4/,J, Med. Chem., 48:2388-2406 (2005).
Trumpp-Kallmeyer et al. Development of a Binding Model to Protein Tyrosine Kinases for Substituted Pyrido[2,3-d]pyrimidine Inhibitors. J. Med. Chem. 41(11):1752-1763 (Apr. 28, 1998).
U.S. Appl. No. 15/613,853 Office Action dated Jan. 18, 2019.
Van Tine, B.A., et al., ER and PI3K Independently Modulate Endocrine Resistance in ER-PositiveBreast Cancer, Cancer Discovery, vol. 1, No. 4, Sep. 1, 2011 (Sep. 1, 2011), pp. 287-288, XP055145623. ISSN: 2159-8274, DOI: 10.1158/2159-8290.CD-11-0192.
Wistuba, Ignacio I., et al., Methodological and practical challenges for personalized cancer therapies, Nature Rev. Clinical Oncology, 2011, Nature Publishing Group, vol. 8, pp. 135-141.
Anonymous: "NCT02311946—A Pilot Study to Investigate the Effect of Concurrent Antacid Administration on the Bioavailability of Six Expermental formulations of Palbociclib" retried from the internet: https://clinicaltrials.gov/ct2/show/NCT02311946—May 28, 2015.
Mitra, et al., "Impaired Drug Absorption Due to High Stomach pH: A Review of Strategies for Mitigation of Such Effect to Enable Pharmaceutical Product Development", Mol. Pharm., vol. 10, No. 11, pp. 3970-3979.
Office Action dated May 18, 2020, for JP Application No. 2018551527.

\* cited by examiner

PHARMACEUTICAL FORMULATION OF PALBOCICLIB AND A PREPARATION METHOD THEREOF

CROSS-REFERENCE

This application is a continuation of Ser. No. 16/554,112 filed Aug. 28, 2019, issued as patent no. 10,813,937 on Oct. 27, 2020, which is a continuation application of Ser. No. 15/613,853 filed Jun 5, 2017, issued as U.S. Pat. No. 10,449,195 on Oct. 22, 2019, which is a continuation application of PCT/CN2016/086546 filed Jun. 21, 2016, which claims the benefit of priority to CN 201610187046.8 filed Mar. 29, 2016, each of which is entirely incorporated herein by reference.

TECHNICAL FIELD

The present invention belongs to the pharmaceutical field. More specifically, the present invention relates to a pharmaceutical formulation of palbociclib and a preparation method thereof. The palbociclib of the present invention may be a palbociclib free base or any of its pharmaceutically acceptable salts.

BACKGROUND ART

World Health Organization statistics show that breast cancer is the world's second cause of cancer deaths in women. Over the past few decades, the incidence of breast cancer showed an increasing trend. It is expected that by 2020, there will be more than 1.7 million new cases of breast cancer each year. By 2012, there are 1.67 million new cases of breast cancer worldwide, accounting for 25% of all new cases of cancer, wherein 883,000 cases are in developed countries and 794,000 cases are in developing countries. The growth rate of new cases of breast cancer in developing countries is slightly higher than that in developed countries. There are 522,000 cases of breast cancer deaths, ranking fifth in lethality rate in all cancers. In underdeveloped areas, the breast cancer causes 324,000 women deaths, accounting for 14.3% of all cases of cancer deaths, and is the most frequent lethal cancer. In developed areas, there are 198,000 cases of breast cancer deaths in women, accounting for 15.4% of all cases of cancer deaths, second only to lung cancer. Therefore, breast cancer is still one of the world's important health problems.

According to the international patent WO2003/062236, palbociclib is an inhibitory agent for cyclin-dependent kinases (CDKs) 4 and 6, which inhibits the synthesis of DNA primarily by preventing cells from G1 phase to S phase via the inhibition of CDK4/6 activity, and can be used to treat metastatic breast cancer. Clinical trial studies have shown that palbociclib combined with letrozole is very effective in postmenopausal patients with locally infiltrating breast cancer or in newly diagnosed estrogen receptor (ER)-positive and HER-2-negative patients. Its chemical structure is as follows:

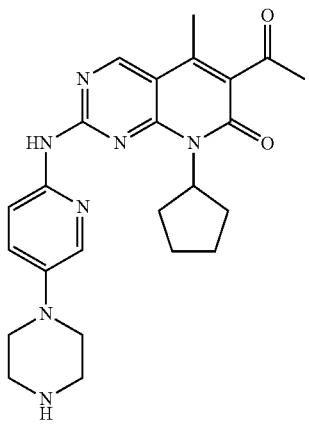

The structure and preparation method of said compound and its salts have been described in the international patent WO2003/062236 and U.S. Pat. No. 6,936,612. The preparation methods of free bases and salts of various acids are also described in the international patent application WO2005/005426 and U.S. Pat. Nos. 7,345,171 and 7,863,278. According to the description in the international patent application WO2005/005426, the solubility of the palbociclib free base in water is poor, which leads to a low bioavailability and is disadvantageous for the absorption in human body. The free base has a strong adhesive property upon impact, and said adhesive property is related to the specific surface area of the particles, so its particle size must be controlled in a certain range. According to the international patent application WO2014128588, it is necessary to use an active pharmaceutical ingredient (API) of palbociclib free base having a larger particle size in order to improve the physichemical properties and the capacity to produce a formulation product. If the palbociclib free base is reacted with an acid to generate salts so as to increase the solubility, the salts have a poor solid nature and thereby are disadvantageous for being developed as a solid formulation, according to the reports in the previously known patents.

At the same time, palbociclib is an insoluble drug. At present, palbociclib has been approved for sale in the United States. According to the instructions for the approved product of palbociclib in the United States, one of seven patients has poor absorption upon administration of the palbociclib product. For these patients, the efficacy of said product will be relatively low. It is likely that the poor solubility of the drug causes the poor absorption in some patients. Thus, in the present, it is very necessary to further improve the dosage form of palbociclib so as to increase the dissolution rate and bioavailability thereof.

SUMMARY OF THE INVENTION

It is an object of the present invention to develop a novel pharmaceutical product for improving the dissolution and bioabsorption of palbociclib. According to the prior art and common knowledge, it is generally considered that the in vitro dissolution of an oral solid formulation product of an insoluble drug has a certain correlation with its in vivo absorption. Thus, an in vitro dissolution method is employed in the present invention to assess the capacity of the formulation product to be absorbed in vivo.

The present invention has surprisingly found that the dissolution of the oral solid formulation product prepared by mixing the API of palbociclib with a pharmaceutically acceptable acidic auxiliary material and optionally adding another pharmaceutically acceptable excipient can be significantly increased relative to the oral solid formulation products prepared in the prior art.

The present invention has also surprisingly found that, the disadvantage that the API having a small particle size cannot be used for the preparation of formulations as disclosed in the international patent application WO2014128588 can be overcome by pulverizing the API of palbociclib to reduce its particle size to D90 at 20 μm or less and then mixing with a pharmaceutically acceptable acidic auxiliary material, or by mixing the API of palbociclib with the pharmaceutically acceptable acidic auxiliary material, co-pulverizing to reduce the particle size of the mixture to D90 at 20 μm or less, and optionally adding another pharmaceutically acceptable excipient; and after an oral dosage form is prepared, the in vitro dissolution can be significantly increased.

The present invention has also surprisingly found that the API of palbociclib and the pharmaceutically acceptable acidic auxiliary material can be co-dissolved in a solvent and the concentration of the API of palbociclib in the solvent can be up to 50 mg/ml or more; and when a hydrophilic high-molecular material is further added and dissolved evenly and the solvent is removed by volatilization, an amorphous solid dispersion is formed. After an oral solid formulation product is prepared by optionally further adding another pharmaceutically acceptable excipient, its dissolution is further significantly increased.

The present invention has also surprisingly found that the method for preparing a solid dispersion of the present invention can also convert the acidic auxiliary material into an amorphous state and the amorphous state can be maintained for a long period of time, which is advantageous for maintaining the amorphous state of the API of palbociclib.

In the invention, by adding the acidic auxiliary material, reducing the particle size of the API of palbociclib and making the palbociclib in an amorphous manner, the in vitro dissolution of palbociclib is increased, and thereby its in vivo bioavailability can be improved.

In particular, the present invention provides a pharmaceutical formulation of palbociclib, which comprises a palbociclib free base or a pharmaceutically acceptable salt thereof and an acidic auxiliary material.

In one embodiment, the palbociclib free base or the salt thereof is a solid.

In one embodiment, the particle size (D90) of palbociclib in the pharmaceutical formulation is 20 μm or less.

In one embodiment, the particle size (D90) of palbociclib and the acidic auxiliary material in the pharmaceutical formulation is 20 μm or less.

In one embodiment, the acidic auxiliary material is one or more selected from the group consisting of a pharmaceutically acceptable water-soluble organic acid or a hydrate or an acidic salt thereof, a water-soluble acidic amino acid or a hydrate or an acidic salt thereof, an acidic salt of a water-soluble amino acid or a hydrate thereof, or an acidic salt of a water-soluble inorganic acid or a hydrate thereof.

In one embodiment, the water-soluble organic acid is one or more selected from the group consisting of tartaric acid, fumaric acid, succinic acid, citric acid, lactic acid and malic acid; the water-soluble acidic amino acid is one or more selected from the group consisting of glutamic acid and aspartic acid; the acidic salt of a water-soluble amino acid is one or more selected from the group consisting of the acidic salts of glycine, alanine and serine; and the acidic salt of the water-soluble inorganic acid is one or more selected from the group consisting of dihydric phosphate and bisulfate.

In one embodiment, the acidic auxiliary material is preferably one or more selected from the group consisting of tartaric acid, fumaric acid, succinic acid, citric acid, lactic acid and malic acid, more preferably tartaric acid.

In one embodiment, the mass ratio of the acidic auxiliary material to palbociclib is from 0.2:1 to 5:1, preferably from 0.5:1 to 2:1.

In one embodiment, the pharmaceutical formulation is a tablet or capsule.

In one embodiment, the dosage of the tablet or capsule is from 25 mg to 500 mg, preferably from 50 mg to 150 mg.

The present invention also provides a solid dispersion of palbociclib, which comprises a palbociclib free base or a pharmaceutically acceptable salt thereof, an acidic auxiliary material and a hydrophilic high-molecular material.

In one embodiment, the hydrophilic high-molecular material is one or more selected from the group consisting of povidone K30 (PVP-K30), copovidone VA64 (PVP-VA64), Soluplus, hydroxypropylmethylcellulose E5 (HPMC-E5), hydroxypropylmethylcellulose acetate succinate (HPMC-AS -HF), hydroxypropyl-β-cyclodextrin and sulfobutylether-β-cyclodextrin.

In one embodiment, the acidic auxiliary material is selected from one or more pharmaceutically acceptable organic acids and optionally one or more pharmaceutically acceptable inorganic acids. Among them, the pharmaceutically acceptable organic acid is preferably selected from the group consisting of tartaric acid, fumaric acid, succinic acid, citric acid, lactic acid, malic acid, aliphatic sulfonic acids (e.g., methanesulfonic acid, ethanesulfonic acid, isethionic acid, etc.) and aromatic sulfonic acids (e.g., benzenesulfonic acid, p-toluenesulfonic acid, etc.), and the pharmaceutically acceptable inorganic acid is preferably selected from the group consisting of hydrochloric acid, sulfuric acid, phosphoric acid and the like. In the present invention, "optionally" means that the pharmaceutically acceptable inorganic acid can be present or absent and, if the pharmaceutically acceptable inorganic acid is present, the amount of the pharmaceutically acceptable organic acid can be reduced.

In one embodiment, the mass ratio of the hydrophilic high-molecular material to palbociclib is from 0.1:1 to 10:1, and the mass ratio of the acidic auxiliary material to palbociclib is from 0.2:1 to 5:1; preferably, the mass ratio of the hydrophilic high-molecular material to palbociclib is from 1:1 to 3:1, and the mass ratio of the acidic auxiliary material to palbociclib is from 0.5:1 to 2:1.

The present invention also provides a method for the preparation of a pharmaceutical formulation, comprising: mixing an API of palbociclib with a pharmaceutically acceptable acidic auxiliary material, preferably at a certain mass ratio, and further, optionally adding another pharmaceutically acceptable excipient.

The present invention also provides another method for the preparation of a pharmaceutical formulation, comprising: pulverizing the API of palbociclib to control the particle size at 20 μm or less, and then mixing with the pharmaceutically acceptable acidic auxiliary material, or adding the acidic auxiliary material to the API, mixing and co-pulverizing to control the particle size at 20 μm or less; and further, optionally adding another pharmaceutically acceptable excipient.

The present invention also provides a method for the preparation of a solid dispersion, comprising: mixing palbociclib with an acidic auxiliary material; adding a solvent (including but not limited to water, ethanol, acetone and a mixture thereof, preferably water or a mixture thereof with other solvents, e.g. the mixture of water and ethanol, the mixture of water and acetone, etc.) for dissolving or dispersing; adding a hydrophilic high-molecular material, dissolving or dispersing evenly; and removing the solvent by heating, for example, evaporating the solvent to dry by vacuum drying or heating drying or freeze drying or other drying ways, in order to achieve the purpose of dispersing the drug in the high-molecular solid carrier to a high degree, so as to prepare the solid dispersion.

In the preparation of the solid dispersion of the present invention, the concentration of the API of palbociclib in the solvent (e.g., water) can be up to 50 mg/ml or more, thereby improving the preparation efficiency of the solid dispersion.

The present invention also provides the use of a pharmaceutical formulation or a solid dispersion for the treatment of breast cancer.

In the present invention, palbociclib refers to a palbociclib free base or a pharmaceutically acceptable salt thereof, which can be used interchangeably.

For those skilled in the art, the excipient is well known and may be an adhesive, a filler, a disintegrant, a lubricant, a preservative, an antioxidant, a flavoring agent, a fragrance, a cosolvent, an emulsifier, a solubilizer, an osmotic pressure regulator, a coloring agent and the like.

In the present invention, palbociclib is pulverized, or the palbociclib is mixed with the acidic auxiliary material and co-pulverized, for example, by means of the airflow pulverization technique, in order to reduce the particle size to D90 at 20 μm or less.

In the present invention, the pharmaceutical formulation is an oral solid formulation product, such as a tablet or a capsule. Such a product is generally prepared by mixing the API with another pharmaceutically acceptable auxiliary material, such as an excipient, a lubricant, a disintegrant and the like, so as to prepare the oral solid formulation product. The palbociclib oral solid formulation product which has been approved for sale in the United States (the trade name is Ibrance), was manufactured by the above-mentioned technique, according to the description in its drug instructions.

The present invention successfully prepares the solid dispersion of palbociclib for the first time by means of a special combination. In the prior art, the solid dispersion is a kind of formulation technique, and useful for a formulation product of an insoluble drug. Usually, an amorphous solid dispersion is prepared from the insoluble API together with a hydrophilic pharmaceutical high-molecular auxiliary material. The methods for the preparation of the amorphous solid dispersion include a solvent method and a melting method. The solvent method includes dissolving the API and the auxiliary material together in a solvent and then volatilizing the solvent. The melting method includes co-melting the API and the high-molecular auxiliary material and rapidly cooling the same. In view of the high melting point of palbociclib, reaching 271° C., and the insolubility in most of solvents, it is impossible to prepare the amorphous solid dispersion in accordance with the solid dispersion technique in the prior art.

In the present invention, the formulation prepared by mixing the API of palbociclib with the acidic auxiliary material exhibits a cumulative dissolution rate of 47.8% in a dissolution medium at pH 6.0 for 60 minutes, increased from 34.0% of the product prepared by the prior formulation technique (FIG. 1).

Further, the formulation prepared by pulverizing palbociclib (having a particle size at 20 μm or less, FIG. 2), or the formulation prepared by mixing and co-pulverizing palbociclib and the acidic auxiliary material exhibits a further increased cumulative dissolution rate of 66.6% and 68.7%, respectively, at pH 6.0 for 60 minutes (FIG. 3).

Further, the solid dispersion prepared by mixing the API of palbociclib with the acidic material and then with the hydrophilic high-molecular material, exhibits a dynamic solubility of 85%, increased from 58% of the API of palbociclib itself, as shown in a dynamic solubility test performed in a buffer at pH 6.0 with stirring for 60 minutes (FIG. 4).

The preparation method of the solid dispersion of the present invention can also convert the acidic auxiliary material such as tartaric acid into an amorphous state (FIG. 5) and the amorphous state is maintained over one week of storage in a stabilizing box at 40° C./75% RH, which is advantageous for maintaining the amorphous state of the palbociclib solid dispersion for a long period of time.

DESCRIPTION OF DRAWINGS

In order to clearly describe the technical solutions of the present invention, a brief description will be given below with reference to the drawings. It is apparent that these drawings merely represent some specific embodiments described in the present application. The invention includes, but not limited to, the following drawings.

DESCRIPTION OF EMBODIMENTS

To further understand the present invention, preferred embodiments of the present invention will be described below with reference to examples. These descriptions are merely illustrative for features and advantages of the novel pharmaceutical formulation of the present invention, without limiting the scope of the present invention.

Example 1

Preparation of the Capsule Dosage Form from the Acidic Auxiliary Material and Palbociclib by Dry Granulation and Filling 1500 mg of the API of palbociclib, 345 mg of lactose, 1200 mg of tartaric acid, 840 mg of microcrystalline cellulose, 210 mg of sodium carboxymethyl starch and 84 mg of silica were weighed and mixed in a three dimensional mixer for 15 minutes, then 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured at pH 6.0 and at the selected time points of 5, 10, 15, 20, 30, 45 and 60 minutes.

At the same time, a comparative test without the acidic auxiliary material was performed in parallel. 1500 mg of the API of palbociclib, 1545 mg of lactose, 840 mg of microcrystalline cellulose, 210 mg of sodium carboxymethyl starch and 84 mg of silica were weighed and mixed in a three dimensional mixer for 15 minutes, then 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured by a basket method at pH 6.0, at a rotation speed of 100 rpm and at the selected time points of 5, 10, 15, 20, 30, 45 and 60 minutes.

Figure 1:
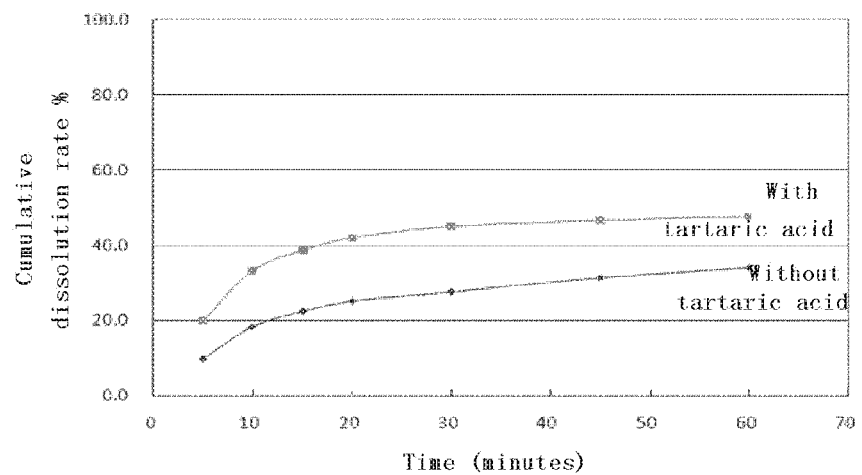
FIG. 1 shows the in vitro dissolution of the capsule formulation prepared from palbociclib with the acidic auxiliary material or without the acidic auxiliary material.
Figure 2:
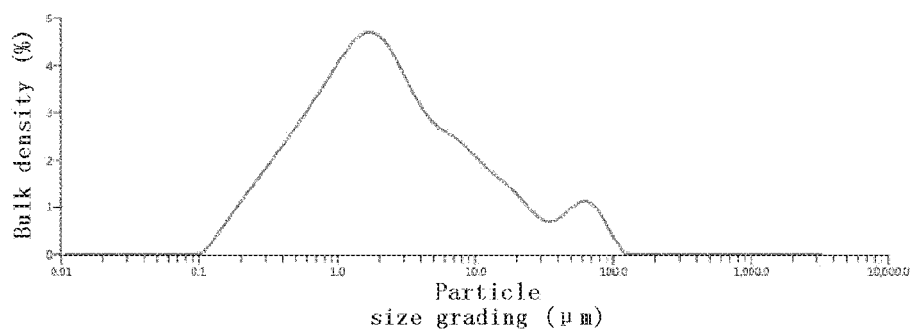
FIG. 2 shows the particle size of the pulverized palbociclib.

The measurement results of the dissolution of the capsules with the acidic auxiliary material and without the acidic auxiliary material were illustrated by the two curves in FIG. 1 respectively.

Example 2

Figure 3:
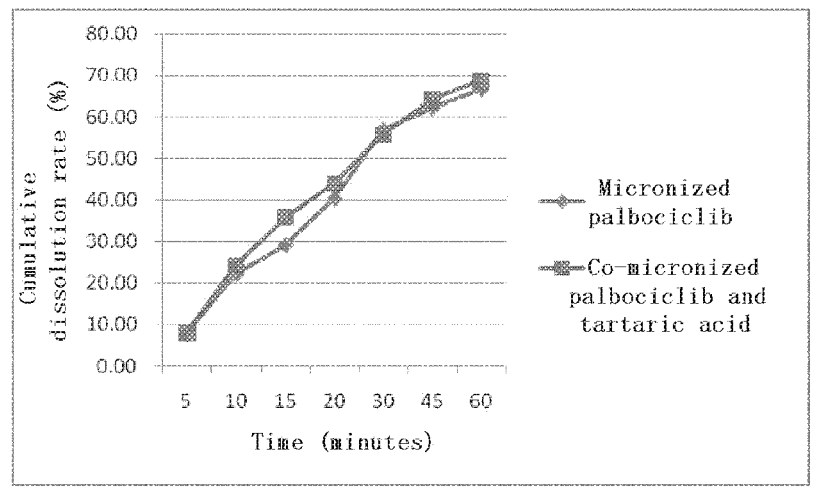
FIG. 3 shows the in vitro dissolution of the capsule formulation prepared by mixing the pulverized palbociclib with the acidic auxiliary material, and of the capsule formulation prepared by co-pulverizing the API of palbociclib and tartaric acid to reduce the particle size.

Preparation of a Capsule by Mixing the Acidic Material with Palbociclib, Followed by Pulverization, and Dry Granulation and Filling 1500 mg of the API of palbociclib, which had been pulverized by airflow, was weighed and mixed with 1200 mg of tartaric acid, 345 mg of lactose, 840 mg of microcrystalline cellulose, 210 mg of sodium carboxymethyl starch and 84 mg of silica in a three dimensional mixer for 15 minutes. Then, 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured by a basket method at pH 6.0, at a rotation speed of 100 rpm and at the selected time points of 5, 10, 15, 20, 30, 45 and 60 minutes. The airflow co-pulverized mixture of the API of palbociclib and tartaric acid (comprising 1500 mg of palbociclib and 1200 mg of tartaric acid) was added with 345 mg of lactose, 840 mg of microcrystalline cellulose, 210 mg of sodium carboxymethyl starch and 84 mg of silica, and mixed in a three dimensional mixer for 15 minutes. Then, 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured by a basket method at pH 6.0, at a rotation speed of 100 rpm and at the selected time points of 5, 10, 15, 20, 30, 45 and 60 minutes. The dissolution results of the formulation prepared by pulverizing palbociclib alone and of the formulation prepared by co-pulverizing palbociclib and tartaric acid were shown in FIG. 3.

Example 3

Preparation of a Solid Dispersion by Mixing Palbociclib with the Acidic Material and Then with PVP-K30

100 mg of the API of palbociclib and 200 mg of tartaric acid were weighed and placed into a 10 ml penicillin bottle, added with 2 ml of purified water, mixed and dissolved. 200 mg of PVP-K30 (manufactured by BASF, Germany, full name: povidone K30) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 4

Preparation of a Solid Dispersion by Mixing Palbociclib with the Acidic Material and Then with a Solid Carrier PVP-VA64

100 mg of the API of palbociclib and 200 mg of tartaric acid were weighed and placed into a 10 ml penicillin bottle, added with 2 ml of double distilled water, mixed and dissolved. 200 mg of PVP-VA64 (manufactured by BASF, Germany, full name: Copovidone) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight for 18 hours at 40° C., and removed the next day, and thereby, the solid dispersion was prepared.

Example 5

Preparation of a Solid Dispersion by Mixing Palbociclib with the Acidic Material and Then with a Solid Carrier Soluplus 100 mg of the API of palbociclib and 200 mg of tartaric acid were weighed and placed into a 10 ml penicillin bottle, added with 2 ml of double distilled water, mixed and dissolved. 200 mg of Soluplus (manufactured by BASF, Germany, full name: polyethylene caprolactam-polyvinyl acetate-polyethylene glycol graft copolymer) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 6

Preparation of a Solid Dispersion by Mixing Palbociclib with the Acidic Material and Then with a Solid Carrier HPMC-E5

100 mg of the API of palbociclib and 200 mg of tartaric acid were weighed and placed into a 10 ml penicillin bottle, added with 2 ml of double distilled water, mixed and dissolved. 200 mg of HPMC-E5 (manufactured by BASF, Germany, full name: hydroxypropylmethylcellulose E5) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 7

Preparation of a Solid Dispersion by Mixing Palbociclib with the Acidic Material and Then with a Solid Carrier HPMC-AS-HF 100 mg of the API of palbociclib and 200 mg of tartaric acid were weighed and placed into a 10 ml penicillin bottle, added with 2 ml of double distilled water, mixed and dissolved. 200 mg of HPMC-AS-HF (manufactured by BASF, Germany, full name: hydroxypropylmethylcellulose AS-HF) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 8

Preparation of a Solid Dispersion by Mixing Palbociclib with the Acidic Material and Hydrochloric Acid and Then with a Solid Carrier PVP VA64

125 mg of the API of palbociclib was weighed and placed into a 10 ml penicillin bottle; 1.991 ml of double distilled water and 8.63 μl of 36% hydrochloric acid solution (having a density of 1.18 g/mL) were added, so that the molar ratio of hydrochloric acid to the API of palbociclib was 1:1. Then 200 mg of tartaric acid was added and completely mixed and dissolved under the action of ultrasound. 100 mg of PVP VA64 was added to the above solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40 ° C., and removed the next day, and thereby, the solid dispersion was prepared.

Example 9

Preparation of a Solid Dispersion by Mixing Palbociclib with the Acidic Material and Phosphoric Acid and Then with a Solid Carrier PVP VA64

125 mg of the API of palbociclib was weighed and placed into a 10 ml penicillin bottle; 2 ml of double distilled water and 27.3 mg of phosphoric acid were added, so that the molar ratio of phosphoric acid to the API of palbociclib was 1:1. Then 200 mg of tartaric acid was added and completely mixed and dissolved under the action of ultrasound. 100 mg of PVP VA64 was added to the above solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 10

Figure 6:
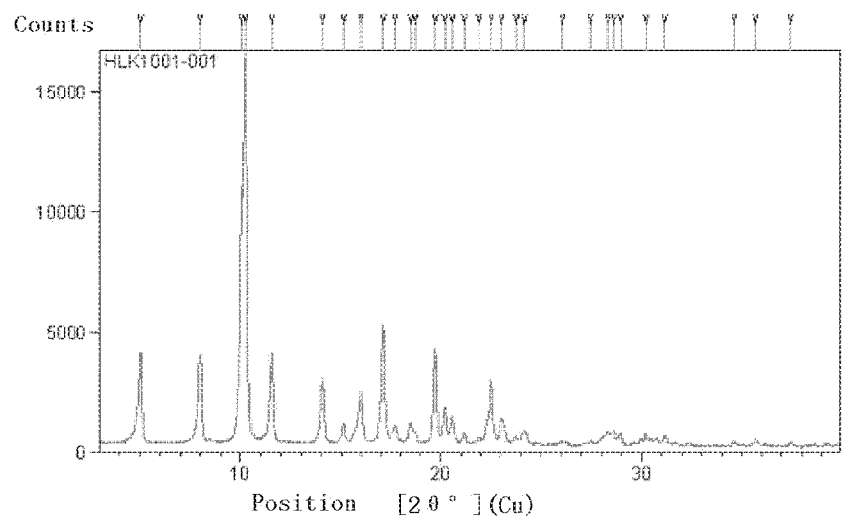
FIG. 6 shows an XRPD pattern of the API of palbociclib used in the present invention.
Figure 9:
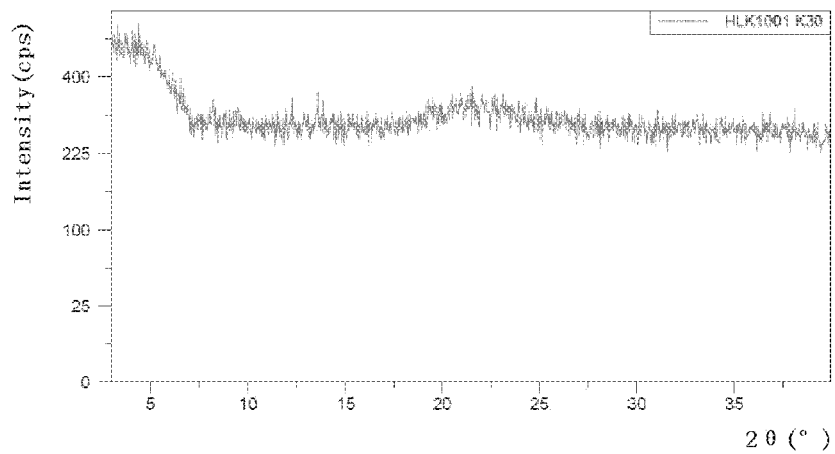
FIG. 9 shows an XRPD pattern of a palbociclib solid dispersion prepared with PVP-K30.

The palbociclib solid dispersion prepared with PVP-K30 in Example 3 and the API of palbociclib both were sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range ($2\theta°$): 3-40; scanning step ($2\theta°$): 0.0263; scanning time (seconds): 46.665; K-Alpha wavelength (Å): 1.54060; K-Alpha2 wavelength (Å): 1.54443; Power setting: 40 mA, 45 kV. The obtained XRPD pattern of the API of palbociclib was shown in FIG. 6; and the XRPD pattern of the solid dispersion prepared with PVP-K30 was shown in FIG. 9.

Example 11

Figure 8:
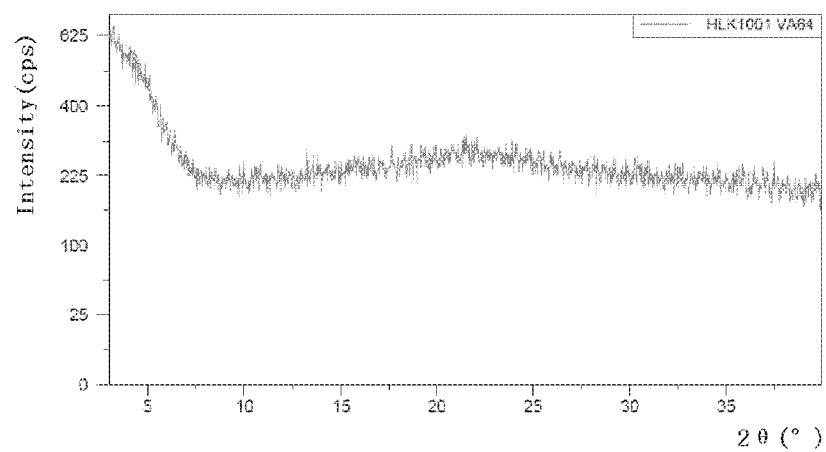
FIG. 8 shows an XRPD pattern of a palbociclib solid dispersion prepared with PVP-VA64.

The palbociclib solid dispersion prepared with PVP-VA64 in Example 4 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range ($2\theta°$): 3-40; scanning step ($2\theta°$):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 8.

Example 12

Figure 10:
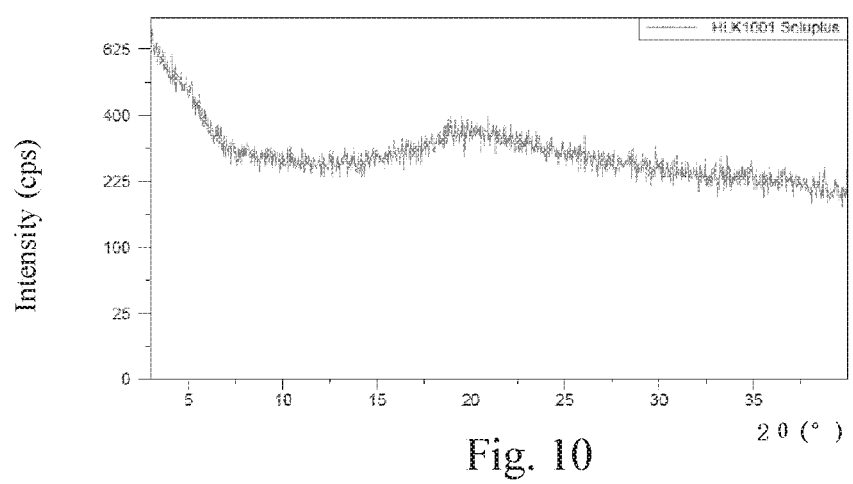
FIG. 10 shows an XRPD pattern of a palbociclib solid dispersion prepared with Soluplus.

The palbociclib solid dispersion prepared with Soluplus in Example 5 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 10.

Example 13

Figure 11:
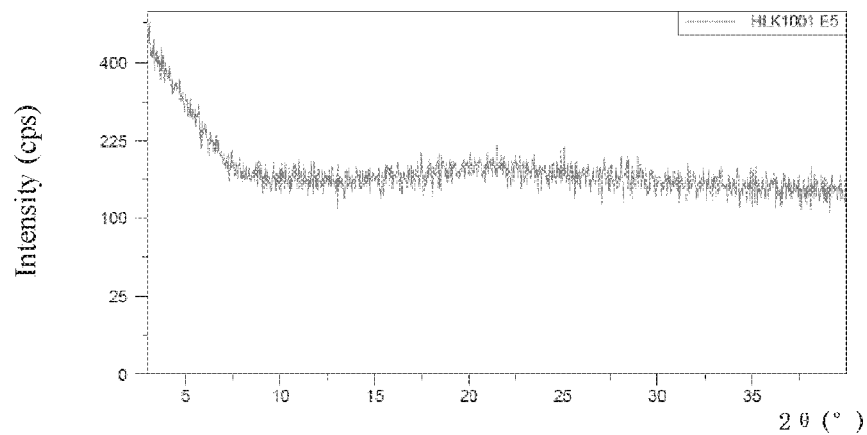
FIG. 11 shows an XRPD pattern of a palbociclib solid dispersion prepared with HPMC-E5.

The solid dispersion prepared with HPMC-E5 in Example 6 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 11.

Example 14

Figure 7:
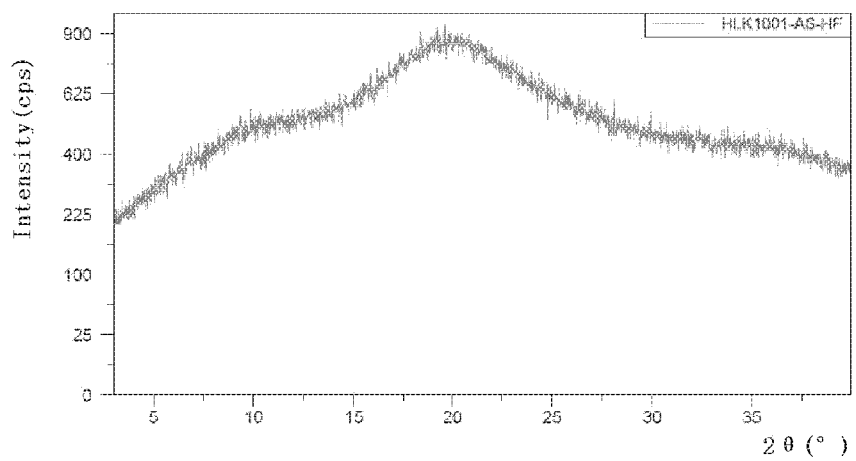
FIG. 7 shows an XRPD pattern of a palbociclib solid dispersion prepared with HPMC-AS-HF.

The solid dispersion prepared with HPMC-AS-HF in Example 7 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 7.

Example 15

Figure 4:
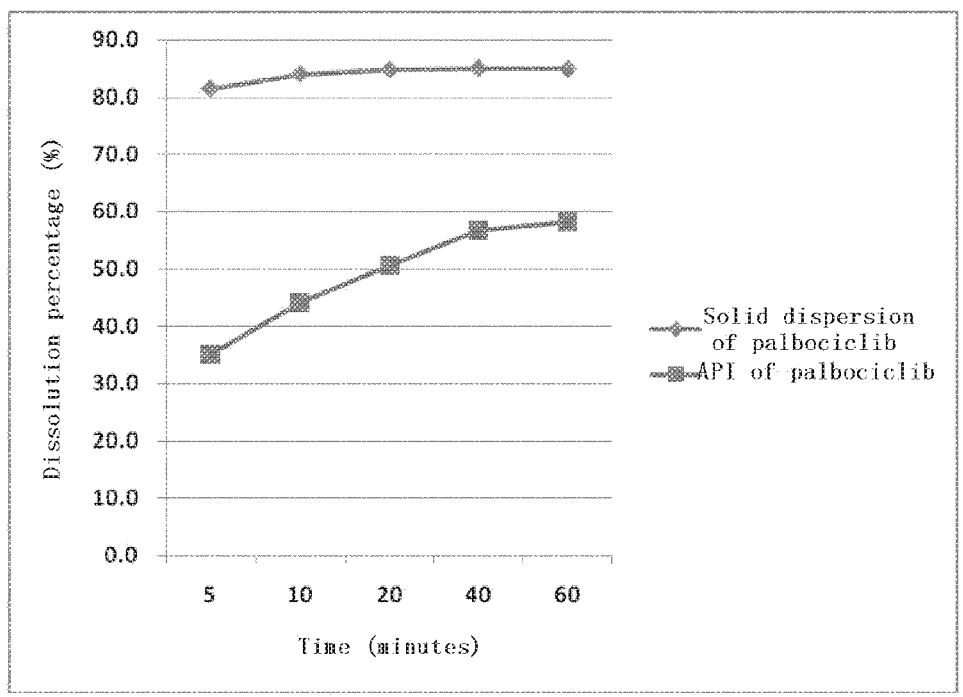
FIG. 4 shows the dynamic solubility of the solid dispersion prepared by mixing the API of palbociclib with the acidic material and then with a hydrophilic high-molecular material, compared to the API of palbociclib itself, as tested in a buffer at pH 6.0 with stirring for 60 minutes.
Figure 5:
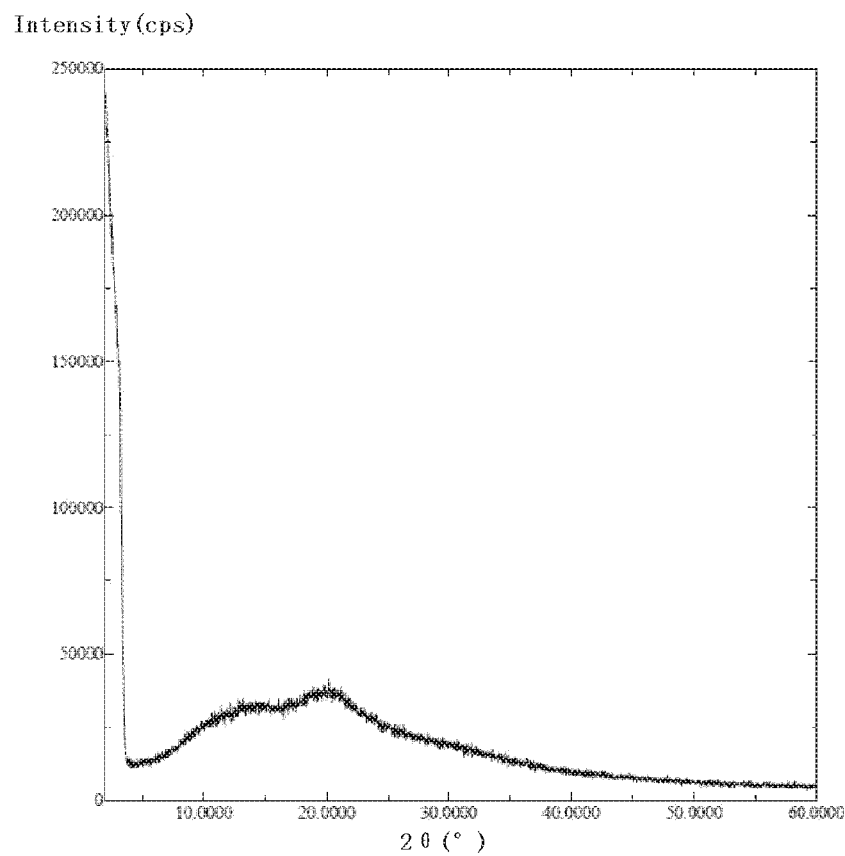
FIG. 5 shows the amorphous state of the acidic auxiliary material tartaric acid in the solid dispersion of the present invention.

62.5 mg of the solid dispersion prepared in Example 3 (containing 12.5 mg of the API of palbociclib in proportion) and 12.5 mg of the API of palbociclib were weighed separately, placed into two 100 ml beakers, respectively, and marked with T1 and T2. 90 ml of phosphate buffer (pH 6.0) was added to the two beakers respectively and a magnetic stir bar was placed therein. The two beakers were placed on a magnetic stirrer separately. 1 ml of the solution was removed separately from each of the beakers at the time points of 5, 10, 20, 40, and 60 minutes and filtered through a 0.45 μm micro PES polyethersulfone filter membrane. The filtrate was analyzed by high performance liquid chromatography, the content of the API of palbociclib was determined and the dissolution percentage was calculated. The results were shown in FIG. 4.

The description of the above examples is only intended to help understanding the central concept of the present invention. It should be noted that those skilled in the art may make improvements and modifications to the novel formulation and its preparation method according to the present invention without departing from the principles of the present invention, and such improvements and modifications also fall within the scope of protection of the claims in the present invention.

The invention claimed is:
1. A composition, wherein the composition comprises:
an amorphous solid dispersion, wherein the amorphous solid dispersion comprises the following in an amorphous state:
palbociclib or a pharmaceutically acceptable salt thereof;
an acidic auxiliary material comprising at least two pharmaceutically acceptable acids, wherein the pharmaceutically acceptable salt of the palbociclib comprises one of the at least two pharmaceutically acceptable acids; and
a hydrophilic high-molecular weight material.
2. The composition of claim 1, wherein the composition is in the dosage form of a tablet or a capsule.
3. The composition of claim 1, wherein the palbociclib or the pharmaceutically acceptable salt thereof is present in an amount of 25 to 500 mg.
4. The composition of claim 1, wherein the palbociclib or the pharmaceutically acceptable salt thereof is present in an amount of 25, 50, 75, 100, 125, 150, or 500 mg.
5. The composition of claim 1, wherein at least one of the at least two pharmaceutically acceptable acids is selected from the group consisting of hydrochloric acid, sulfuric acid, phosphoric acid, and combinations thereof.
6. The composition of claim 1, wherein the at least two pharmaceutically acceptable acids comprise tartaric acid and an inorganic acid.
7. The composition of claim 1, wherein the hydrophilic high-molecular weight material is one or more selected from the group consisting of povidone K30, copovidone VA64, polyethylene caprolactam-polyvinyl acetate-polyethylene glycol graft copolymer, hydroxypropylmethylcellulose E5, hydroxypropylmethylcellulose acetate succinate, hydroxypropyl-β-cyclodextrin and sulfobutyl ether-β-cyclodextrin.
8. The composition of claim 1, wherein the hydrophilic high-molecular weight material is copovidone VA64 or hydroxypropylmethylcellulose E5.
9. A method for treating breast cancer, comprising:
administering to a subject having breast cancer a pharmaceutical composition, wherein the pharmaceutical composition comprises an amorphous solid dispersion, wherein the amorphous solid dispersion comprises the following in an amorphous state:
palbociclib or a pharmaceutically acceptable salt thereof;
an acidic auxiliary material comprising at least two pharmaceutically acceptable acids, wherein the pharmaceutically acceptable salt of the palbociclib comprises one of the at least two pharmaceutically acceptable acids; and
a hydrophilic high-molecular weight material.
10. The method of claim 9, wherein the pharmaceutical composition is orally administered.
11. The method of claim 9, wherein the palbociclib or the pharmaceutically acceptable salt thereof is present in an amount of 25 to 500 mg.
12. The method of claim 9, wherein the palbociclib or the pharmaceutically acceptable salt thereof is present in an amount of 25, 50, 75, 100, 125, 150, or 500 mg.
13. The method of claim 9, wherein at least one of the at least two pharmaceutically acceptable acids is selected from the group consisting of hydrochloric acid, sulfuric acid, phosphoric acid, and combinations thereof.
14. The method of claim 9, wherein the at least two pharmaceutically acceptable acids comprise tartaric acid and an inorganic acid.
15. The method of claim 9, wherein the hydrophilic high-molecular weight material is one or more selected from the group consisting of povidone K30, copovidone VA64, polyethylene caprolactam-polyvinyl acetate-polyethylene glycol graft copolymer, hydroxypropylmethylcellulose E5, hydroxypropylmethylcellulose acetate succinate, hydroxypropyl-β-cyclodextrin and sulfobutyl ether-β-cyclodextrin.

16. The method of claim 9, wherein the hydrophilic high-molecular weight material is copovidone VA64 or hydroxypropylmethylcellulose E5.

17. The composition of claim 5, wherein at least one of the at least two pharmaceutically acceptable acids is hydrochloric acid or phosphoric acid.

18. The composition of claim 17, wherein a molar ratio of the hydrochloric acid or phosphoric acid to the palbociclib or a pharmaceutically acceptable salt thereof is 1:1.

19. The method of claim 13, wherein at least one of the at least two pharmaceutically acceptable acids is hydrochloric acid or phosphoric acid.

20. The method of claim 19, wherein a molar ratio of the hydrochloric acid or phosphoric acid to the palbociclib or a pharmaceutically acceptable salt thereof is 1:1.

* * * * *